United States Patent [19]
Blight et al.

[11] Patent Number: 6,012,342
[45] Date of Patent: Jan. 11, 2000

[54] PLUNGER ASSEMBLY FOR MEASURING OCCLUSION PRESSURE ON A FLEXIBLE TUBE

[75] Inventors: David D. Blight; Frank L. Caruso; Stephan L. Williams, all of Arvada, Colo.

[73] Assignee: Cobe Cardiovascular Operating Co., Inc., Arvada, Colo.

[21] Appl. No.: 08/998,845

[22] Filed: Dec. 29, 1997

[51] Int. Cl.⁷ .................. G01L 1/04; F16K 7/04; E03B 11/00
[52] U.S. Cl. .............. 73/862.621; 251/7; 251/4; 137/595
[58] Field of Search ............... 73/700, 862.621, 73/862.65, 862.48, 118.1, 141 R; 604/250; 251/4, 5, 7, 14; 137/595

[56] References Cited

U.S. PATENT DOCUMENTS

| | | |
|---|---|---|
| 3,092,995 | 6/1963 | Glerum . |
| 3,938,380 | 2/1976 | Karlsson ................ 73/141 R |
| 4,078,625 | 3/1978 | Loeb ........................ 177/233 |
| 4,102,295 | 7/1978 | Crook, Jr. et al. . |
| 4,170,163 | 10/1979 | Payne . |
| 4,267,725 | 5/1981 | Roth et al. ............ 73/862.65 |
| 4,399,685 | 8/1983 | Atkey . |
| 4,492,575 | 1/1985 | Mabille . |
| 4,596,374 | 6/1986 | Thompson et al. . |
| 4,759,226 | 7/1988 | Leurer .................. 73/862.48 |
| 4,960,259 | 10/1990 | Sunnanvader et al. ........ 604/250 |
| 4,993,456 | 2/1991 | Sule . |
| 5,036,714 | 8/1991 | Christoffers et al. . |
| 5,083,454 | 1/1992 | Yopp ........................ 73/118.1 |
| 5,190,071 | 3/1993 | Sule . |
| 5,433,244 | 7/1995 | Sule . |
| 5,445,613 | 8/1995 | Orth . |
| 5,520,057 | 5/1996 | Nakamura ............. 73/862.621 |
| 5,569,866 | 10/1996 | Allison ................... 73/862.621 |

*Primary Examiner*—Benjamin R. Fuller
*Assistant Examiner*—Robin Clark
*Attorney, Agent, or Firm*—Popovich & Wiles, P.A.

[57] ABSTRACT

A plunger assembly for obstructing the flow of fluid through a flexible tube is provided. The assembly comprises a plunger sleeve member having a first open end and a compression mechanism for selectively contacting and compressing the flexible tube. The compression mechanism has a contacting portion for contacting the flexible tube and an extending portion with the extending portion being slidably receivable within the plunger sleeve member through the first open end of the plunger sleeve member. A spring mechanism is mounted about the extending portion of the compression mechanism and between the contacting portion of the compression mechanism and the first open end of the plunger sleeve member for providing selective movement to the compression mechanism relative to the plunger sleeve member. A sensor mechanism associated with the plunger sleeve and the compression mechanism is provided for translating the displacement of the compression means relative to the plunger sleeve to a measurement of force applied by the compression means to the flexible tube.

24 Claims, 3 Drawing Sheets

PLUNGER ASSEMBLY FOR MEASURING OCCLUSION PRESSURE ON A FLEXIBLE TUBE

BACKGROUND OF THE INVENTION

1. Field of the Invention

This invention relates generally to a pressure sensitive plunger assembly for compressing a tube to obstruct the flow of fluid flowing through the tube and, more particularly, it relates to a pressure sensitive plunger assembly for compressing a tube to obstruct the flow of fluid flowing through the tube which measures the occlusion resistance pressure on the tube to reliably indicate full closure of the tube.

2. Description of the Prior Art

In the prior art, clamping devices for clamping resilient tubes to temporarily and periodically prevent fluid from flowing through the tube are well-known. Such clamping devices are often used in association with medical equipment, and are frequently used in connection with medical apparatus which perform circulation of fluids to or from a living body. Of course, clamping devices are also associated with a variety of other products in many different fields.

Clamping devices take various forms, but typically function by manually or electrically inducing engagement of a structure which pinches the tube at a particular location thereby reducing or completely preventing passage of fluid through the tube. Some clamping devices are connected to a mechanism for detecting a specific condition in the fluid which, when the condition occurs, activates the clamping or unclamping of the tube. For example, it may be desirable to terminate blood flow through a tube if the hematocrit level falls above or below a certain value. In this instance, if the hematocrit level drops, as sensed by a detection means, an electrical signal is relayed to the clamping device causing it to close off the tube. Similarly, it may be desirable to terminate blood flow through a tube on the detection of air entrained in the blood.

Many clamping devices currently in use are capable of accommodating only those flexible tubes having a small internal diameter (approximately one (1) millimeter to twelve and one-half (12.5) millimeters (approximately ½ inch)) and which are very pliable. Furthermore, many clamping devices currently in use maintain either a fully opened or a fully closed condition. That is, the tube positioned within the clamp may be either completely uncompressed (open tube) or completely compressed (closed tube), but can not be partially compressed. Such clamping devices do not provide incrementally increasing compression of the tube as required by some medical procedures. In addition, many clamping devices do not provide a mechanism for manually operating the clamping device under emergency situations, such as a power failure, or as may be dictated by medical necessity.

In an effort to overcome some of the shortcomings of the previous clamping structures, the Orth, U.S. Pat. No. 5,445, 613, describes a clamping device having a clamping structure and a plunger. The plunger has a plunger end and a plunger shaft connected to the plunger end. The Orth patent's clamping device obstructs the flow of fluid through a tube by electrically or manually actuating the plunger end of the plunger against the tube in response to an electrical signal from a condition detection mechanism associated with the tube. The plunger of the clamping device of the Orth patent can also be actuated to compress the tube gradually, providing incrementally decreasing flow through the tube.

While the clamping device of the Orth patent obstructs the flow of fluid through a tube, there are several disadvantages with the Orth patent's clamping device. First, the clamping device of the Orth patent merely measures the positional displacement of the plunger relative to the clamping surface. Plunger position alone, however, is an unreliable analog for detecting full tube closure since there are many variables, i.e., tube size and valve positioning, which could cause the tube not to be fully occlude even when the plunger is at the "fully occluded" position. Furthermore, since the occlusion of the tube is directly related to the pressure generated by the rebound of the tube against the plunger, merely measuring the positional displacement of the tube greatly affects the accuracy of the clamping device on tubes having a variety of elasticities. The Orth patent's clamping device is not capable of measuring the occlusion pressure exerted by the plunger on the tube.

Second, the plunger shaft and the condition detection mechanism of the clamping device of the Orth patent are not sealed from the elements. Debris or the like entering into clamping device of the Orth Patent can adversely affect the movement of the plunger and/or the activation of the condition detection mechanism such that the clamping device fails to occlude the tube the proper amount.

Accordingly, there exists a need for a pressure sensitive plunger assembly for occluding a tube which can be used on variety of different tubes having a variety of different durometers. Additionally, a need exists for a pressure sensitive plunger assembly for occluding a tube which measures the amount of occlusion pressure exerted on the tube for reliably indicating full closure of the tube. Moreover, there exists a need for a pressure sensitive plunger assembly for occluding a tube which is sealed from the elements to inhibit debris and the like from entering within the plunger assembly and adversely affecting the operation of the plunger assembly.

SUMMARY OF THE INVENTION

The present invention is a plunger assembly for occluding the flow of fluid through a flexible tube. The assembly comprises a plunger sleeve member having a first open end and compression means for selectively contacting and compressing the flexible tube. The compression means has a contacting portion for contacting the flexible tube and an extending portion with the extending portion being slidably receivable within the plunger sleeve member through the first open end of the plunger sleeve member. Spring means are mounted about the extending portion of the compression means and between the contacting portion of the compression means and the first open end of the plunger sleeve member for providing selective movement to the compression means relative to the plunger sleeve member. Sensor means are associated with the plunger sleeve and the compression means for translating the displacement of the compression means relative to the plunger sleeve to a measurement of force applied by the compression means to the flexible tube.

In an embodiment of the present invention, the plunger assembly further comprises a stationary anvil positioned nearingly adjacent the flexible tube with the flexible tube being selectively compressed between the compression means and the anvil. Preferably, the plunger sleeve is movable relative to the tube.

In another embodiment of the plunger assembly of the present invention, the compression means comprises a plunger tip having a first contacting end and a second mounting end and a plunger body having a first mounting end and a second free end. The first contact end of the plunger tip is contactable with the tube for selective compression of the tube and the second mounting end of the plunger tip is connected to the first mounting end of the plunger body with the second free end of the plunger body being slidably receivable within the plunger sleeve member through the first open end of the plunger sleeve member. Preferably, the first contacting end of the plunger tip is beveled thereby minimizing the area of contact between the plunger tip and the tube.

In yet another embodiment of the plunger assembly of the present invention, the spring means is an elastomeric washer. Preferably, the elastomeric washer effectively seals the extending portion of the compression means and the sensor means.

In still another embodiment of the plunger assembly of the present invention, the sensor means comprises a magnet and means for determining the relative position of the magnet. The magnet is mounted to the extending portion of the compression means and the determining means is mounted to the plunger sleeve member. Preferably, the determining means comprises a Hall effect sensor.

In yet still another embodiment of the plunger assembly of the present invention, the magnet is mounted to the plunger sleeve member and the determining means is mounted to the extending portion of the compression means. Preferably, the determining means comprises a Hall effect sensor.

The present invention further includes a method for occluding a flexible tube to obstruct the flow fluid through the flexible tube. The method comprises providing a plunger assembly and an anvil with the plunger assembly having a plunger sleeve and a plunger tip, providing spring means between the plunger sleeve and the plunger tip, positioning the flexible tube between the plunger tip and the anvil, mounting spring means between the between the plunger sleeve and the plunger tip for providing selective movement to the compression means relative to the plunger sleeve member, moving the plunger sleeve in a direction generally away from the tube causing the plunger tip to simultaneously move in a direction generally away from the tube, and translating the displacement of plunger tip relative to the plunger sleeve into a measurement of force applied by the plunger tip on the flexible tube.

In an embodiment of the present invention, the plunger tip has a tip portion and a shaft portion and the method further comprises mounting the spring means about the shaft portion and inserting at least a portion of the shaft portion into the plunger sleeve.

In another embodiment of the present invention, the method further comprises positioning a stationary anvil nearingly adjacent the flexible tube and compressing the flexible tube between the compression means and the anvil.

In yet another embodiment of the present invention, the method further comprises beveling the plunger tip thereby minimizing the area of contact between the plunger tip and the tube.

In still another embodiment of the present invention, the spring means is an elastomeric washer.

In still yet another embodiment of the present invention, the sensor means comprises a magnet and means for determining the relative position of the magnet and the method further comprises mounting the magnet to the plunger tip and mounting the determining means to the plunger sleeve. In a further embodiment of the present invention, the method comprises mounting the magnet to the plunger sleeve member and mounting the determining means to the plunger tip.

DETAILED DESCRIPTION OF THE PREFERRED EMBODIMENTS

Figure 1:
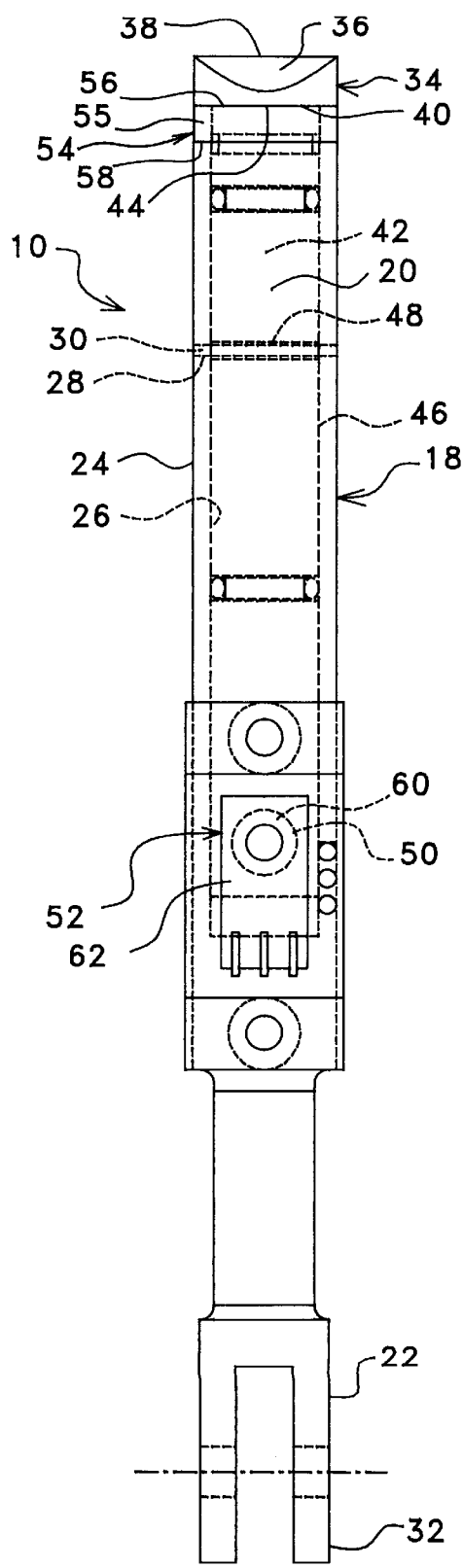
FIG. 1 is a front view illustrating the plunger assembly for measuring occlusion pressure on a flexible tube constructed in accordance with the present invention.
Figure 3:
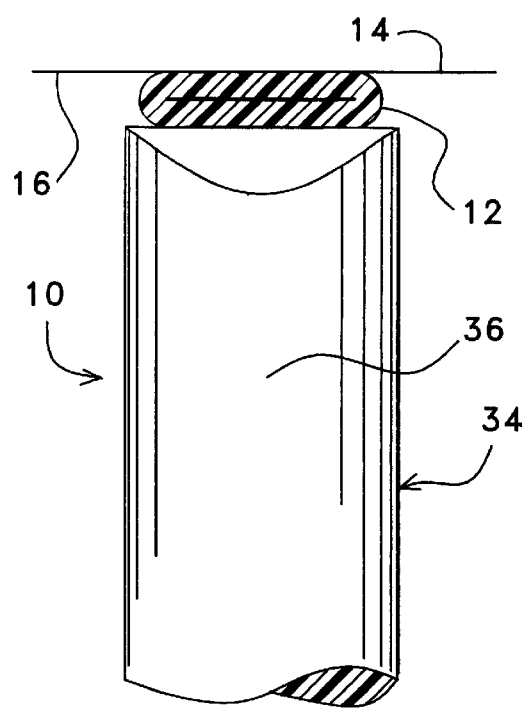
FIG. 3 is a front view illustrating a plunger tip of the plunger assembly for measuring occlusion pressure on a flexible tube with the flexible tube being completely occluded by the plunger tip.
Figure 4:
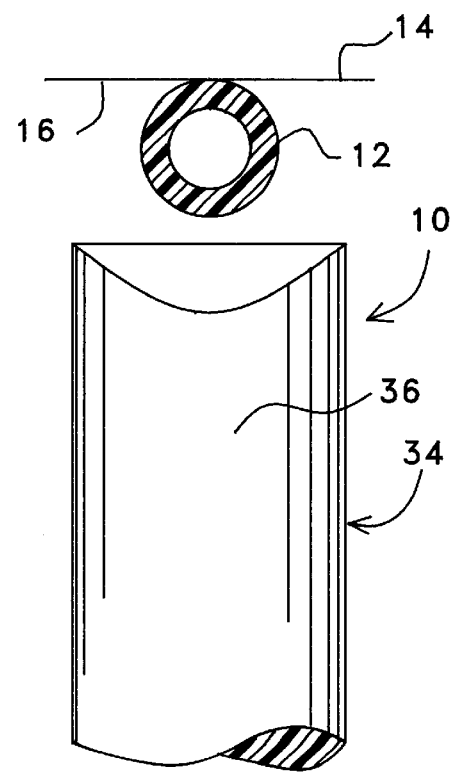
FIG. 4 is a front view illustrating a plunger tip of the plunger assembly for measuring occlusion pressure on a flexible tube with the flexible tube being completely open.

As illustrated in FIG. 1, the present invention is a plunger assembly, indicated generally at 10, for measuring occlusion pressure on a flexible tube 12, as illustrated in FIGS. 3 and 4, for detection of full occlusion of the flexible tube. The flexible tube 12 is compressible between the plunger assembly 10 and against an anvil member 14 (FIGS. 3 and 4) to obstruct the flow of fluid (not shown) through the flexible tube 12. The flexible tube 12 is generally constructed from a resilient material such as soft plastic which allows the flexible tube 12 to maintain a generally tubular shape upon release of the plunger assembly 10, as illustrated in FIG. 4 on the flexible tube 12. As illustrated in FIGS. 3 and 4, the anvil member 14 is generally constructed from a rigid material and has a substantially smooth, flat surface 16 nearingly adjacent the flexible tube 12 allowing the flexible tube 12 to be completely occluded, as illustrated in FIG. 3, between the plunger assembly 10 and the flat surface 16 of the anvil member 14.

In general, the plunger assembly 10 of the present invention is typically associated with medical apparatus (not shown) for closing off flexible tubes through which the fluid, such as blood, flows. It should be noted that while the plunger assembly 10 of the present invention has been and will be described as being associated with medical apparatus which perform circulation of fluids to or from a living body and blood salvage, it is within the scope of the present invention to utilize the plunger assembly 10 with any type of resilient tube for any reason, not limited to medical apparatus. Actual operation of the plunger assembly 10 on the flexible tube 12 against the flat surface 16 of the anvil member 14 will be discussed in further detail below.

Figure 2:
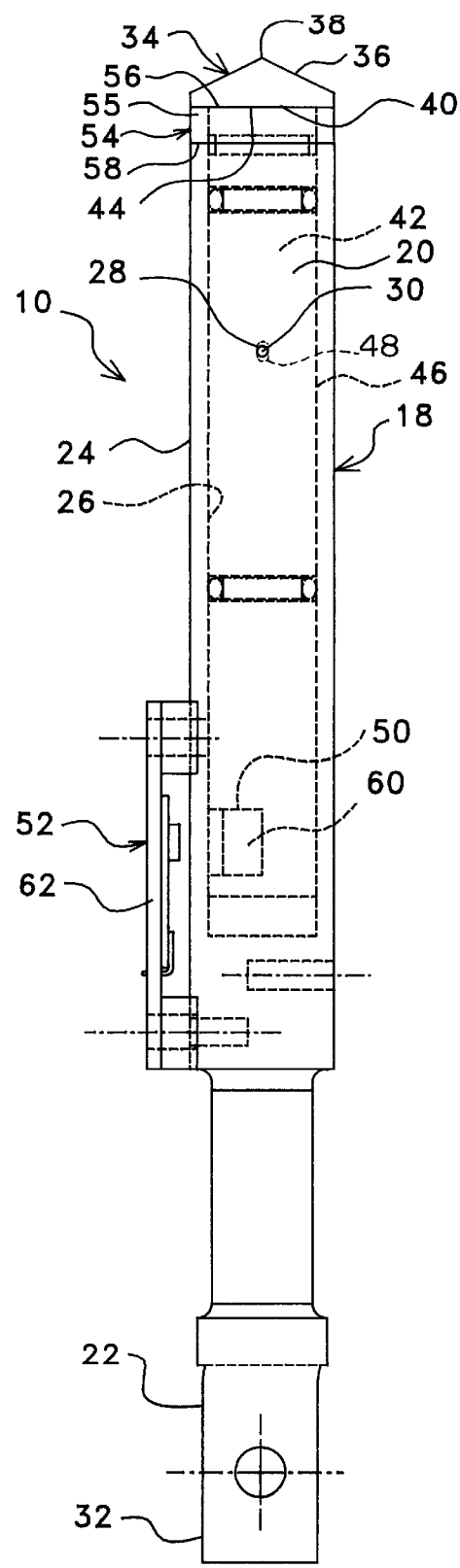
FIG. 2 is a side view illustrating the plunger assembly for measuring occlusion pressure on a flexible tube constructed in accordance with the present invention.

As illustrated in FIGS. 1 and 2, the plunger assembly 10 of the present invention has a substantially cylindrical plunger sleeve 18 constructed from a non-corrosive material such as stainless steel or the like. The plunger sleeve 18 has a first open end 20, a second end 22 opposite the first end 20, an outer surface 24 having a diameter $d_1$, and an inner surface 26 having a diameter $d_2$. The plunger sleeve 18 further has an aligned sleeve pin receiving aperture 28 formed through the outer surface 24 and the inner surface 26 for receiving a securing pin 30 as will be described in further detail below. Furthermore, the second end 22 of the plunger sleeve 18 has linkage means 32 connectable to an actuator (not shown) such as a solenoid or motor driven cam.

The plunger assembly 10 of the present invention further has a plunger tip 34 constructed from a non-corrosive material such as stainless steel or the like. The plunger tip 34 has a tip portion 36 having a first tube contacting end 38 and a second mounting end 40, and a shaft member 42 having a first mounting end 44 and a second free end 46. The tip portion 36 preferably has a diameter $d_3$ that is substantially equal to the diameter $d_1$ of the outer surface 24 of the plunger sleeve 18. Furthermore, the shaft member 42 preferably has an outer diameter $d_4$ which is less than the diameter $d_2$ of the inner surface 26 of the plunger sleeve 18 allowing at least a portion of the shaft member 42 to be freely receivable within the plunger sleeve 18 as will be described in further detail below.

The first tube contacting end 38 of the tip portion 36 is designed and constructed to be contactable with the flexible tube 12 to completely occlude the flexible tube 12 against the flat surface 16 of the anvil member 14. Preferably, the first tube contacting end 38 is beveled thereby minimizing the surface contact area between the tip portion 36 of the plunger tip 34 and the flexible tube 12. It should be noted, however, while the first tube contacting end 38 of the tip portion 36 has been described as being beveled, it is within the scope of the present invention to have a first tube contacting end having other shapes and configurations.

The first mounting end 44 of the shaft member 42 is substantially rigidly mounted to the second mounting end 40 of the tip portion 36 of the plunger tip 34. It should be noted that the first mounting end 44 of the shaft member 42 can be mounted to the tip portion 36 by welding or other means, or, in the alternative, the plunger tip 34, including the shaft member 42 and the tip portion 36, can be constructed from a unitary piece of non-corrosive material and machined to form the shaft member 42 and the tip portion 36.

The second free end 46 of the shaft member 42 is slidably receivable within the plunger sleeve 18 for free, unfettered movement of the plunger tip 34 relative to the plunger sleeve 18. The second free end 46 of the shaft member 42, like the plunger sleeve 18, further has an oval shaft pin receiving aperture 48 formed completely through the shaft member 42 for receiving the securing pin 30. Furthermore, the second free end 46 of the shaft member 42 has a hollowed area 50 for receiving a portion of a sensor mechanism 52 as will be discussed in further detail below.

The plunger assembly 10 of the present invention further has a spring mechanism 54, such as a compliant, compressible washer 55, positioned between the tip portion 36 of the plunger tip 34 and the first end 20 of the plunger sleeve 18. In the preferred embodiment of the spring mechanism 54 comprising the washer 55, the washer 55 has a first end 56 and a second end 58 opposite the first end 56 and is preferably constructed from a compressible resilient material such as rubber or the like. While being described as being constructed from a resilient material such as rubber or the like, it should be noted that other resilient materials for construction of the washer 55 are also within the scope of the present invention, as well as a compression (wire) spring, belleville washers, and coil springs, for example.

The washer 55 preferably has an outer diameter $d_5$ substantially equal to the diameter $d_1$ of the outer surface 24 of the plunger sleeve 18 and the diameter $d_3$ of the tip portion 36 of the plunger tip 34. Furthermore, the washer 55 preferably has an inner diameter $d_6$ slightly less than the diameter $d_4$ of the shaft member 42 of the plunger tip 34 thereby allowing the washer 55 to snugly fit about the shaft member 42 inhibiting movement of the washer 55 relative to the shaft member 42.

Figure 5:
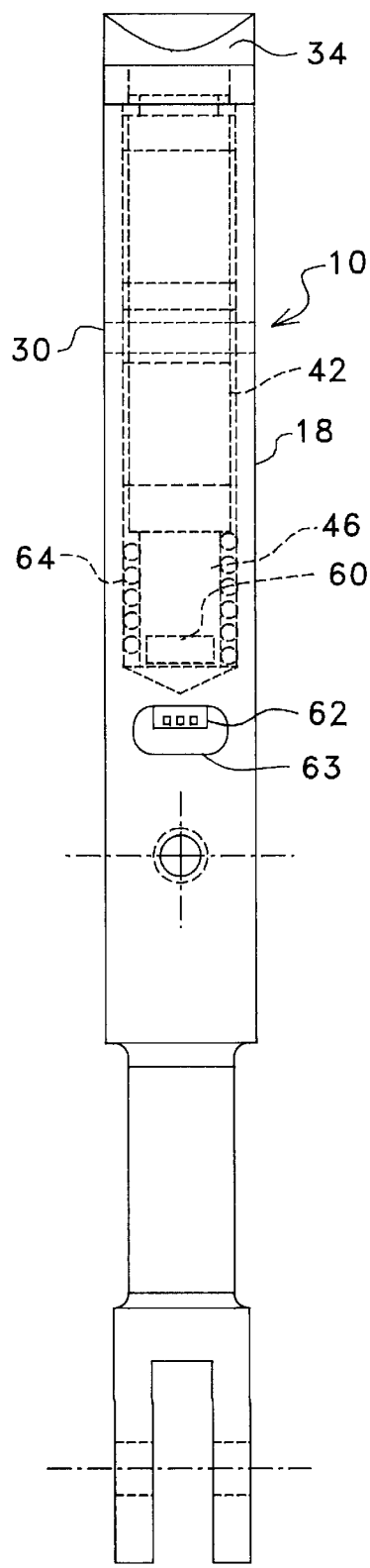
FIG. 5 is a front view illustrating another embodiment of the plunger assembly for measuring occlusion pressure on a flexible tube constructed in accordance with the present invention.
Figure 6:
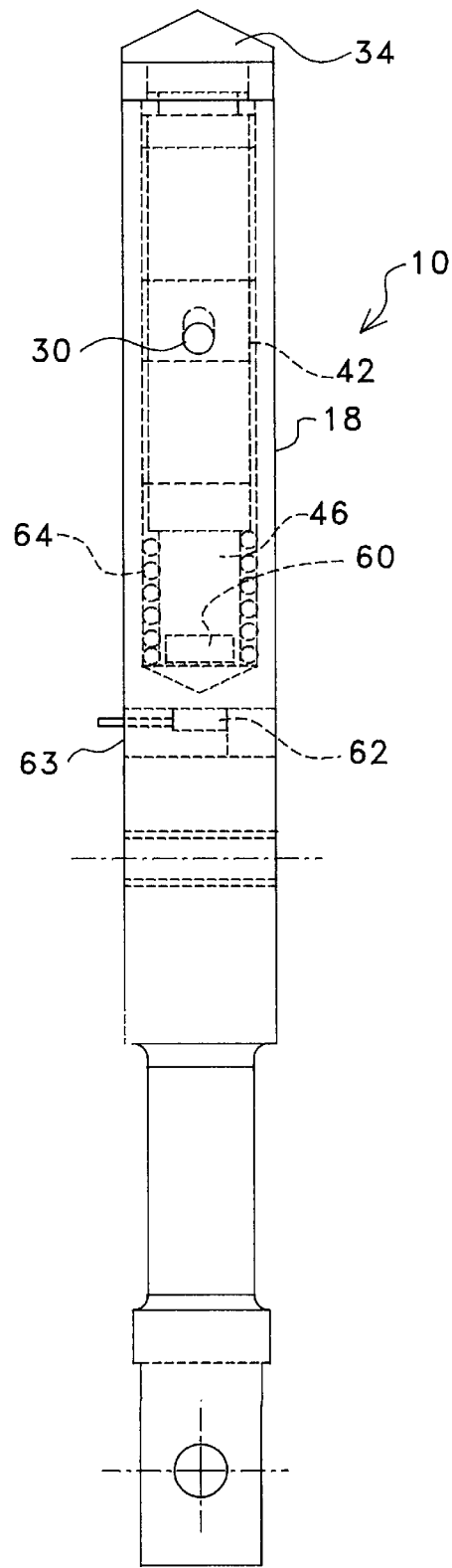
FIG. 6 is a side view illustrating the embodiment as illustrated in FIG. 5 of the plunger assembly for measuring occlusion pressure on a flexible tube constructed in accordance with the present invention.

To construct the plunger assembly 10 of the present invention, the washer 55 is positioned about the shaft member 42 and manipulated such that the washer 55 is positioned about the first mounting end 44 of the shaft member 42 nearingly adjacent the second mounting end 40 of the tip portion 36 of the plunger tip 34. The friction between the washer 55 and the shaft member 42 maintains the desired position of the washer 55 relative to the plunger tip 34. Next, in an alternative embodiment as illustrated in FIGS. 5 and 6, a compression spring 64 is positioned within the plunger sleeve 18. The compression spring 64 biases the plunger tip 34 in a direction generally toward the flexible tube 12.

Then, in all embodiments of the plunger assembly 10 of the present invention, the shaft member 42 is freely inserted into the first open end 20 of the plunger sleeve 18 until the washer 55 is positioned against both the second mounting end 40 of the tip portion 36 of the plunger tip 34 and the first open end 20 of the plunger sleeve 18. The securing pin 30 is then inserted into the sleeve pin receiving aperture 28 of the plunger sleeve 18 and the shaft pin receiving aperture 48 of the plunger tip 34. Preferably, the diameter of the securing pin 30 is slightly greater than the diameter of the sleeve pin receiving aperture 28 but less than the diameter of the shaft pin receiving aperture 48 to frictionally secure the securing pin 30 within the sleeve pin receiving aperture 28 but allowing axial movement of the plunger tip 34 relative to the plunger sleeve 18 and the shaft pin receiving aperture 48. It is within the scope of the present invention, however, to secure the securing pin 30 within the sleeve pin receiving aperture 28 by other means including, but not limited to, providing threads on the securing pin 30 and corresponding threads within the sleeve pin receiving aperture 28.

The construction of the plunger assembly 10 of the present invention heretofore described effectively seals the shaft member 42 of the plunger tip 34 and the interior of the plunger sleeve 18. Debris or the like is inhibited from entering the plunger assembly 10 thereby ensuring proper operation of the plunger assembly 10 during use.

The plunger assembly 10 of the present invention further comprises the sensor mechanism 52, as briefly mentioned above, for translating the displacement of the plunger tip 34 relative to the plunger sleeve 18 to a measurement of force applied by the plunger tip 34 to the flexible tube 12. As illustrated in FIGS. 1 and 2, the sensor mechanism 52 includes a permanent magnet 60 mounted to the plunger tip 34 and a hall effect sensor 62 positioned on the plunger sleeve 18 nearingly adjacent the permanent magnet 60. As illustrated in FIGS. 5 and 6, in an alternative embodiment of the present invention, the permanent magnet 60 is mounted to the second free end 46 of the shaft member 42 and the hall effect sensor 62 is positioned within a receiving aperture 63 formed in the plunger sleeve 18.

Regardless of the embodiment, the hall effect sensor 62 has appropriate associated electronic circuitry (not shown)

contained on a printed circuit board (not shown) to interpret signal proportional to magnet position as indicative of the occlusion pressure on the flexible tube 12 during use. It should be noted, however, that while the sensor mechanism 52 has been described as having the permanent magnet 60 mounted to the plunger tip 34 and the hall effect sensor 62 mounted on the plunger sleeve 18, it is within the scope of the present invention to have the permanent magnet 60 mounted on the plunger sleeve 18 and the hall effect sensor 62 mounted directly to the plunger tip 34.

While the sensor mechanism 52 of the plunger assembly 10 of the present invention as heretofore been described as being a permanent magnet 60 and a hall effect sensor 62, it is within the scope of the present invention to utilize other sensor mechanisms including, but not limited to, LVDT's and strain gages spanning the area between the plunger sleeve 18 and the plunger tip 34 similar to the permanent magnet 60 and the hall effect sensor 62 as described above.

In operation of the plunger assembly 10 of the present invention, the plunger assembly 10 is positioned adjacent the flexible tube 12, as best illustrated in FIG. 3, such that the plunger tip 34 completely occludes the fluid flowing through the flexible tube 12 and the washer 55 is in a compressed state. Referring back to FIGS. 1 and 2, upon the occurrence of an event in which the amount of fluid flowing within the tube should be increased, the solenoid or motor driven cam is activated to move the plunger sleeve 18 of the plunger assembly 10 in a direction generally away from the flexible tube 12. As the plunger sleeve 18 is moved away from the flexible tube 12, the plunger tip 34 also begins to move away from the flexible tube 12 and the washer 55 begins to uncompress thereby increasing the relative distance between the permanent magnet 60 and the hall effect sensor 62 of the sensor mechanism 52 thereby causing a change in the magnetic field sensed by the hall effect sensor 62. Basically, the change in the magnetic field represents the change in the plunger tip's 34 position relative to the plunger sleeve 18. The sensor mechanism 52, based on the distance between the permanent magnet 60 and the hall effect sensor 62, determines the occlusion pressure of the plunger assembly 10 on the flexible tube 12 and, therefore, accurately and reliably regulates the amount of fluid flowing through the flexible tube 12 and indicates full occlusion of the flexible tube 12 by the plunger tip 34.

Figure 7:
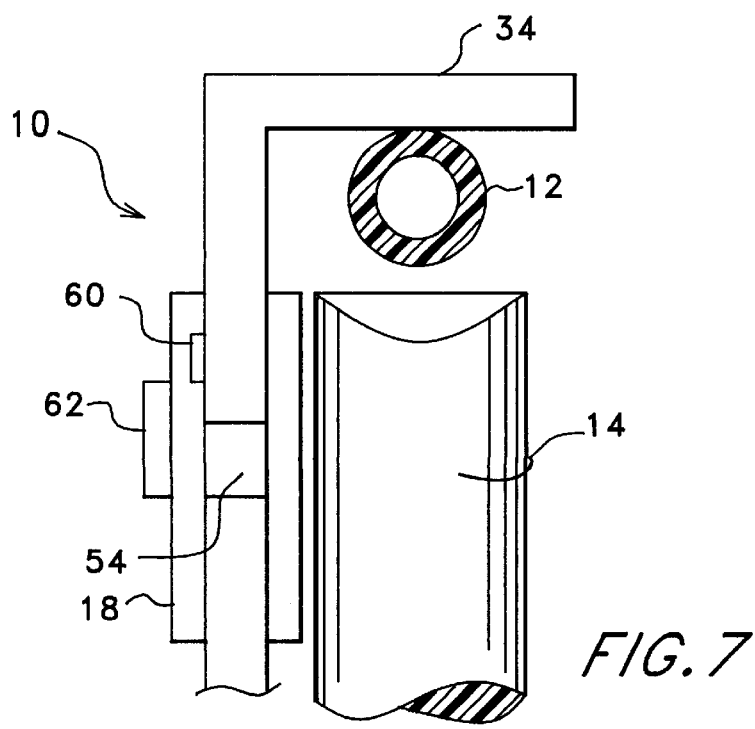
FIG. 7 is a side view illustrating yet another embodiment of the plunger assembly for measuring occlusion pressure on a flexible tube constructed in accordance with the present invention.

In another embodiment of the plunger assembly 10 of the present invention, as illustrated in FIG. 7, rather than pushing the plunger tip 34 to occlude the flexible tube 12 between the plunger tip 34 and the anvil member 14, the plunger tip 34 is pulled toward the anvil member 14 to occlude the flexible tube 12. Rather than deforming in compression as described in the embodiment above, the spring mechanism 54 deforms in tension as the plunger tip 34 is moved toward the anvil member 14. As in the previous embodiments, a permanent magnet 60 is mounted to the plunger tip 34 and a sensor 62 is mounted to the plunger sleeve 18 to determine the occlusion pressure of the plunger tip 34 against the flexible tube 14.

It should be noted that, regardless of the embodiment, since the plunger assembly 10 of the present invention is self-contained, the flat surface 16 of the anvil member 14 does not need to be fixed in relation to the plunger tip 34. The distance between the plunger tip 34 and the anvil member 14 is controlled as a function of pressure and remains the same no matter where the flat surface of the anvil member 14 is positioned.

The plunger assembly 10 of the present invention represents a vast improvement over previous clamping devices in the prior art and can be utilized in a variety of applications such as, for example, flow monitoring in chemical and biological testing and in fluid systems analysis. Since the full occlusion of the flexible tube 12 is directly related to the pressure generated by the rebound of the flexible tube 12, the plunger assembly 10 of the present invention is perfectly suited for use with a variety of flexible tubes having a variety of elasticities. The plunger assembly 10 of the present invention uses the achievement of a sufficiently high occlusion pressure to indicate fall occlusion of the flexible tube 12. Although occlusion pressure is still an analog for full occlusion, occlusion pressure is a much more reliable indicator that the flexible tube 12 is in fact fully occluded as compared to the actual plunger position relative to the flexible tube 12. Furthermore, by sealing the internal workings of the plunger assembly 10 from debris and the like, efficient, reliable use of the plunger assembly 10 in a variety of sterile and non-sterile environments is possible.

The foregoing exemplary descriptions and the illustrative preferred embodiments of the present invention have been explained in the drawings and described in detail, with varying modifications and alternative embodiments being taught. While the invention has been so shown, described and illustrated, it should be understood by those skilled in the art that equivalent changes in form and detail may be made therein without departing from the true spirit and scope of the invention, and that the scope of the present invention is to be limited only to the claims except as precluded by the prior art. Moreover, the invention as disclosed herein, may be suitably practiced in the absence of the specific elements which are disclosed herein.

We claim:

1. An assembly for occluding the flow of fluid through a flexible tube, the assembly comprising:
   an anvil positionable nearingly adjacent the flexible tube; and
   a plunger assembly movable relative to said anvil comprising:
     a plunger sleeve having a first open end;
     compression means for selectively contacting and compressing the flexible tube between said compression means and said anvil, the compression means having a contacting portion for contacting the flexible tube and an extending portion, the extending portion being slidably receivable within the plunger sleeve through the first open end of the plunger sleeve;
     spring means mounted about the extending portion of the compression means and between the contacting portion of the compression means and the first open end of the plunger sleeve for providing selective movement to the compression means relative to the plunger sleeve; and
     sensor means associated with the plunger sleeve and the compression means for translating the displacement of the compression means relative to the plunger sleeve to a measurement of force applied by the compression means to the flexible tube.

2. The assembly of claim 1 wherein said anvil is stationary.

3. The assembly of claim 1 wherein the plunger sleeve is movable relative to the tube.

4. The assembly of claim 1 wherein the compression means comprises a plunger tip having a first contacting end and a second mounting end and a plunger body having a first mounting end and a second free end, the first contacting end of the plunger tip contactable with the tube for selective compression of the tube, the second mounting end of the plunger tip being connected to the first mounting end of the plunger body, and the second free end of the plunger body being slidably receivable within the plunger sleeve through the first open end of the plunger sleeve.

5. The assembly of claim 4 wherein the first contacting end of the plunger tip is beveled thereby minimizing the area of contact between the plunger tip and the tube.

6. The assembly of claim 1 wherein the spring means is an elastomeric washer.

7. The assembly of claim 1 wherein the sensor means comprises a magnet and determining means for generating a signal indicating full closure of the flexible tube based on the relative position of the magnet, the magnet being mounted to the extending portion of the compression means and the determining means being stationarily mounted to the plunger sleeve.

8. The assembly of claim 7 wherein the determining means comprises a Hall effect sensor.

9. The assembly of claim 1 wherein the sensor means comprises a magnet and means for determining the relative position of the magnet, the magnet being mounted to the plunger sleeve and the means for determining being mounted to the extending portion of the compression means.

10. The assembly of claim 9 wherein the determining means comprises a Hall effect sensor.

11. A method for occluding a flexible tube to obstruct the flow fluid through the flexible tube, the method comprising:

providing a plunger assembly and an anvil, the plunger assembly having a plunger sleeve and a plunger tip;

providing spring means between the plunger sleeve and the plunger tip positioning the flexible tube between the plunger tip and the anvil mounting spring means between the plunger sleeve and the plunger tip for providing selective movement to the compression means relative to the plunger sleeve member; and moving the plunger sleeve in a direction generally toward the tube causing the plunger tip to simultaneously move in a direction generally toward the tube; and translating the displacement of plunger tip relative to the plunger sleeve into a measurement of force applied by the plunger tip on the flexible tube.

12. The method of claim 11 wherein the plunger tip has a tip portion and a shaft portion, and further comprising mounting the spring means about the shaft portion and inserting at least a portion of the shaft portion into the plunger sleeve.

13. The method of claim 11 wherein the anvil is stationary and further comprising positioning the stationary anvil nearingly adjacent the flexible tube and compressing the flexible tube between the compression means and the anvil.

14. The method of claim 11 and further comprising beveling the plunger tip thereby minimizing the area of contact between the plunger tip and the tube.

15. The method of claim 11 wherein the spring means is an elastomeric washer.

16. The method of claim 11 wherein the sensor means comprises a magnet and means for generating a signal indicating full closure of the flexible tube based on the relative position of the magnet, and further comprising mounting the magnet to the plunger tip and mounting the determining means to the plunger sleeve.

17. The method of claim 16 wherein the determining means comprises a Hall effect sensor.

18. In a plunger assembly for closure of a flexible tube by compression of said flexible tube between the plunger assembly and an anvil, the improvement comprising:

a plunger sleeve;

a tube contacting member slidably receivable within the plunger sleeve;

spring means mounted between the plunger sleeve and the tube contacting member for providing selective movement to the tube contacting member relative to the plunger sleeve; and sensor means associated with the plunger sleeve and the tube contacting member for translating the displacement of the compression means relative to the plunger sleeve to a measurement of force applied by the tube contacting member to the flexible tube.

19. The improvement of claim 18 wherein said anvil is stationary and is positionable nearingly adjacent the flexible tube, the flexible tube being selectively compressed between the tube contacting member and the anvil.

20. The improvement of claim 18 wherein the plunger sleeve is movable relative to the flexible tube.

21. The improvement of claim 18 wherein the spring means is an elastomeric washer.

22. The improvement of claim 18 wherein the sensor means comprises a magnet and means for generating a signal indicating full closure of the flexible tube based on the relative position of the magnet, the magnet being mounted to the tube contacting member and the determining means being mounted to the plunger sleeve.

23. The improvement of claim 22 wherein the determining means comprises a Hall effect sensor.

24. A plunger assembly for occluding the flow of fluid through a flexible tube, the assembly comprising:

a plunger sleeve having a first open end;

compression means for selectively contacting and compressing the flexible tube, the compression means having a contacting portion for contacting the flexible tube and an extending portion, the extending portion being slidably receivable within the plunger sleeve through the first open end of the plunger sleeve;

an elastometric washer mounted about the extending portion of the compression means and between the contacting portion of the compression means and the first open end of the plunger sleeve for providing selective movement to the compression means relative to the plunger sleeve; and sensor means associated with the plunger sleeve and the compression means for translating the displacement of the compression means relative to the plunger sleeve to a measurement of force applied by the compression means to the flexible tube; wherein, said elastometric washer effectively seals the extending portion of the compression means and the sensor means.

* * * * *